United States Patent
Akasapu et al.

(10) Patent No.: US 11,517,522 B2
(45) Date of Patent: Dec. 6, 2022

(54) APREPITANT READY-TO-USE INJECTION EMULSION COMPOSITIONS

(71) Applicant: Somerset Therapeutics LLC, Hollywood, FL (US)

(72) Inventors: Prem Sagar Akasapu, Somerset, NJ (US); Veerappan Subramanian, Somerset, NJ (US); Ilango Subramanian, Somerset, NJ (US)

(73) Assignee: SOMERSET THERAPEUTICS LLC, Hollywood, FL (US)

( * ) Notice: Subject to any disclaimer, the term of this patent is extended or adjusted under 35 U.S.C. 154(b) by 0 days.

(21) Appl. No.: 17/147,556

(22) Filed: Jan. 13, 2021

(65) Prior Publication Data
US 2021/0212933 A1    Jul. 15, 2021

Related U.S. Application Data

(60) Provisional application No. 62/961,039, filed on Jan. 14, 2020.

(51) Int. Cl.
*A61K 9/00* (2006.01)
*A61K 47/14* (2017.01)
*A61K 9/107* (2006.01)
*A61K 31/5377* (2006.01)
*A61M 5/24* (2006.01)

(52) U.S. Cl.
CPC ............ *A61K 9/0019* (2013.01); *A61K 9/107* (2013.01); *A61K 31/5377* (2013.01); *A61K 47/14* (2013.01); *A61M 5/24* (2013.01)

(58) Field of Classification Search
CPC .... A61K 31/5377; A61K 47/02; A61K 47/10; A61K 47/14; A61K 47/24; A61K 47/26; A61K 9/0019; A61K 9/107; A61M 5/24
See application file for complete search history.

(56) References Cited

U.S. PATENT DOCUMENTS

| | | | |
|---|---|---|---|
| 4,847,296 A * | 7/1989 | Babayan | A61K 31/23 514/552 |
| 9,561,229 B2 * | 2/2017 | Ottoboni | A61K 9/0024 |
| 2017/0119800 A1 * | 5/2017 | Malhotra | A61K 45/06 |

FOREIGN PATENT DOCUMENTS

CN       109364023 A  *   2/2019  .............. A61K 9/107

OTHER PUBLICATIONS

Rull et al. (Medicines for Nausea Jul. 2018 [online] retrieved on Nov. 8, 2021 from: https://patient.info/digestive-health/nausea-and-vomiting/medicines-for-nausea; 6 pages). (Year: 2018).*
Emend® Highlights of Prescribing Information Apr. 2018 [online] retrieved on Jan. 21, 2022 from: https://www.accessdata.fda.gov/drugsatfda_docs/label/2018/022023s017lbl.pdf; 23 pages). (Year: 2018).*
Google translation of CN 109364023A 2019; 12 pages. (Year: 2019).*

* cited by examiner

*Primary Examiner* — Ernst V Arnold
(74) *Attorney, Agent, or Firm* — William D. Hare, Esq.; McNeely, Hare & War, LLP

(57) ABSTRACT

The present invention provides an emulsion composition comprising aprepitant for treatment of emesis. Particularly, the invention is a ready-to-use emulsion compositions comprising aprepitant and medium chain triglycerides for administration by intravenous infusion, wherein the emulsion composition is also free of ethanol. Further, the invention also provides processes of preparing such compositions and their use for the prevention and control of acute and delayed chemotherapy-induced nausea and vomiting, and/or for prevention of postoperative nausea and vomiting.

15 Claims, No Drawings

APREPITANT READY-TO-USE INJECTION EMULSION COMPOSITIONS

FIELD OF THE INVENTION

Disclosed herein are emulsion compositions comprising aprepitant for the treatment of emesis. More specifically, the field of the invention relates to ready-to-use emulsion compositions of aprepitant comprising medium chain triglycerides for intravenous infusion administration, wherein the emulsion compositions are free of ethanol. Further, the field of the invention relates to a process of preparing such compositions and their use for the prevention and control of acute and delayed chemotherapy-induced nausea and vomiting, and/or for the prevention of postoperative nausea and vomiting.

BACKGROUND

Aprepitant (5-([(2R, 3S)-2-((R)-1-[3, 5-bis (trifluoromethyl) phenyl] ethoxy)-3-(4-fluoro-phenyl) morpholino] methyl)-1H-1, 2, 4-triazol-3(2H)-one) is an antiemetic compound that belongs to the class of substance P/neurokinin 1 ($NK_1$) receptor antagonists that mediate their effect by blocking the neurokinin 1 ($NK_1$) receptor. Aprepitant is a selective, high-affinity antagonist at human substance P NK-1 receptors and is manufactured by Merck & Co. and marketed in the United States under the brand name, Emend®. It is available as oral capsules for the prevention and control of acute and delayed chemotherapy-induced nausea and vomiting and for the prevention of postoperative nausea and vomiting.

Aprepitant is a white to off-white crystalline solid, with a molecular weight of 534.43 and with the structure of:

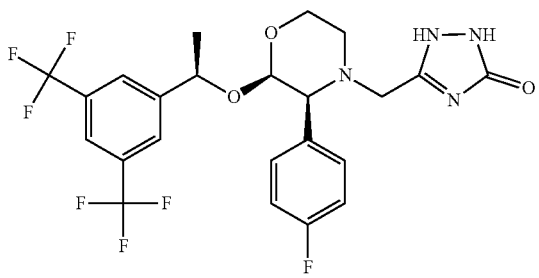 [SMILES: C[C@@H](O[C@H]1OCCN(Cc2nc(=O)[nH][nH]2)[C@H]1c1ccc(F)cc1)c1cc(C(F)(F)F)cc(C(F)(F)F)c1]

Aprepitant is practically insoluble in water, sparingly soluble in ethanol and isopropyl acetate, and slightly soluble in acetonitrile.

Oral formulations of aprepitant are commercially available as a nanoparticulate composition (Emend®, Merck) with an average particle size of less than about 1,000 nm. Although these formulations appear to have been developed to address problems of aprepitant's poor solubility in pharmaceutical compositions, the bioavailability of the compound when given orally is only about 60-65%.

In order to improve aprepitant's solubility, several attempts have been made by solid-state manipulation. For example, WO 2007/088483 teaches the preparation of amorphous aprepitant, while WO 2007/112457 discloses a mixture of two crystalline forms, namely, Form I and Form II, and pharmaceutical compositions thereof. US 2010/0151035 discloses a pharmaceutical composition of aprepitant containing a polymer and inert pellets, whereby the dissolution rate of the drug is dependent on the particle size of the pellets. WO 2007/147160 describes compositions of amorphous aprepitant in the form of a co-precipitate with enhanced solubility of aprepitant. US 2011/0009362 discloses a solubility-enhanced form of aprepitant that involves forming a co-precipitate between the drug and cyclodextrin. However, despite these numerous attempts to increase the solubility of aprepitant, the stability of such compositions in solution is believed to be generally insufficient.

Aprepitant is also available as a water-soluble prodrug salt form (Emend® for injection, Merck), fosaprepitant dimeglumine, for intravenous (IV) administration since aprepitant by itself has limited water solubility. Fosaprepitant is a phosphorylated prodrug form of aprepitant and is rapidly converted to aprepitant after IV administration.

Prodrug formation of the aprepitant molecule involves phosphorylation of the aprepitant molecule followed by salt formation with dimeglumine. Fosaprepitant has been reported to undergo rapid conversion to aprepitant in less than 30 minutes of an IV infusion. Studies have shown the non-inferiority and bioequivalency of fosaprepitant to aprepitant with respect to the prevention and control of acute and delayed chemotherapy-induced nausea and vomiting. However, the additional steps required for the synthesis of fosaprepitant add significant complexity and cost to the drug.

Another means to improve the solubility and permeability of aprepitant is to prepare an emulsion that can be suitable for intravenous administration and also that enhances the bioavailability of aprepitant once administered.

Lipids are commonly used in emulsion preparation for parenteral administration. Such emulsions, generally prepared from soybean or safflower oils, also provide the patients with linoleic acid, an essential fatty acid, and, through its metabolism, arachidonic acid and prostaglandins. The composition of the typical long-chain-triglyceride (LCT) molecule includes fatty acids of 16 and 18 carbons in length with trace amounts of larger fatty acids. LCTs are sometimes defined as having fatty acids of 14 or more carbons in length and include olive oil and soybean oil. Medium chain triglycerides (MCT) generally have fatty acids with less than 14 carbons in length and sometimes are defined as having less than 12 carbons in length.

Heron Therapeutics Inc. developed an aprepitant emulsion formulation using long-chain-triglycerides (soybean oil). This formulation is marketed in the United States under the brand name Cinvanti®. The aprepitant emulsion product is indicated in adults for the prevention of: (1) Acute and delayed nausea and vomiting associated with initial and repeat courses of highly emetogenic cancer chemotherapy (HEC) including high-dose cisplatin as a single-dose regimen; (2) Delayed nausea and vomiting associated with initial and repeat courses of moderately emetogenic cancer chemotherapy (MEC) as a single-dose regimen; and (3) Nausea and vomiting associated with initial and repeat courses of MEC as a 3-day regimen.

Cinvanti® is intravenously administered either as injection over a two (2) minute period or by infusion over a thirty (30) minute period. The administration should be completed approximately 30 minutes prior to chemotherapy. The administration of Cinvanti® via intravenous infusion requires dilution of 18 mL or 14 mL of the emulsion concentrate into an infusion bag containing 100 mL of 0.9% sodium chloride or 5% dextrose resulting in the formation of either a 1.3 mg/mL (0.13% w/v) or 1.0 mg/mL (0.1% w/v) concentration of aprepitant. This diluted emulsion can be stored only for a period of 72 hours under refrigeration. The approved composition of Cinvanti® contains 130 mg Aprepitant, egg lecithin (2.6 g), ethanol (0.5 g), sodium oleate (0.1 g), soybean oil (1.7 g), sucrose (1 g), and water for injection (12 g). The composition appears to be the subject of U.S. Pat. Nos. 9,561,229; 9,808,465; 9,974,742; 9,974,793 and 9,974,794.

Since Cinvanti® is administered in the clinical setting, the dilution step of the existing formulation for administration via intravenous infusion needs additional infrastructure for aseptically transferring the contents of the vials into the bags, however, this preparation may have the potential for contamination with microorganisms. Additionally, the Cinvanti® formulation contains ethanol and therefore is known to occasionally create drowsiness in the recipient upon administration which can limit the person's ability to drive post treatment.

Thus, there exists an enduring need to develop an improved aprepitant emulsion composition that will provide an alternative to existing formulations for non-oral treatment for the intravenous or parenteral administration of aprepitant for treatment of emesis. The inventors of the present invention have prepared an emulsion formulation that allows aprepitant to be incorporated into an emulsion for intravenous administration and remains stable during the shelf life of the formulation. In particular, the inventors of the present invention have developed an emulsion formulation of aprepitant that can be administered without any further dilution by intravenous infusion. This formulation avoids the contamination possibility that may occur during the dilution step. The emulsion composition is also free of ethanol in the formulation and thereby reduces the side effects of ethanol administration. Further, the emulsion can also be terminally sterilized by moist heat to thereby provide greater sterility assurance.

SUMMARY OF THE INVENTION

The present invention provides an emulsion composition comprising aprepitant for the treatment of emesis. In particular, the present invention provides a ready-to-use emulsion formulations of aprepitant for intravenous infusion, wherein the emulsion compositions are also free of ethanol in the formulations. By ready-to-use emulsion, it is understood that the emulsion does not need to be further diluted prior to administration. Therefore, when using the ready-to-use emulsion, the emulsion is administered from its original packaging directly to the patient without a step of dilution. This is in contrast with the Cinvanti® product which is intravenously administered either as injection or infusion wherein intravenous infusion requires dilution of 18 mL or 14 mL of the emulsion concentrate into an infusion bag containing 100 mL of 0.9% sodium chloride or 5% dextrose resulting in the formation of either a 1.3 mg/mL (0.13% w/v) or 1.0 mg/mL (0.1% w/v) concentration of aprepitant. When the ready-to-use emulsion of the invention is infused, the product is not diluted.

In one general aspect, there is provided an emulsion composition comprising about 0.1% to about 0.13% of aprepitant by weight.

In one general aspect, there is provided an emulsion composition comprising about 0.1% to about 0.13% of aprepitant by weight, wherein the emulsion composition is free of an alcohol.

In one general aspect, there is provided an emulsion composition comprising about 0.1% to about 0.13% of aprepitant by weight, wherein the emulsion composition is free of ethanol.

In one general aspect, there is provided an emulsion composition comprising about 0.1% to about 0.13% of aprepitant by weight and about 1% to about 20% of oil by weight, wherein the emulsion composition is free of ethanol.

In one general aspect, there is provided an emulsion composition comprising about 0.1% to about 0.13% of aprepitant by weight, about 1% to about 25% of oil by weight, and about 1% to about 20% of oil by weight.

In one general aspect, there is provided an emulsion composition comprising about 0.1% to about 0.13% of aprepitant by weight, and about 1% to about 20% of medium chain triglycerides by weight.

In one general aspect, there is provided an emulsion composition, wherein the ratio of oil to aprepitant in the composition ranges from about 5:1 to about 200:1 by weight.

In one general aspect, there is provided an emulsion composition comprising about 0.1% to about 0.13% of aprepitant by weight, and about 0.5% to about 5% of emulsifier by weight.

In one general aspect, there is provided an emulsion composition comprising about 0.1% to about 0.13% of aprepitant by weight and about 0.5% to about 5% of lecithin by weight.

In one general aspect, there is provided an emulsion composition, wherein the ratio of emulsifier to aprepitant in the composition ranges from about 3:1 to about 50:1 by weight.

In one general aspect, there is provided an emulsion composition comprising about 0.1% to about 0.13% of aprepitant by weight, about 1% to about 20% of medium chain triglycerides by weight, and about 0.1% to about 7% of tonicity agent by weight.

In one general aspect, there is provided an emulsion composition comprising about 0.1% to about 0.13% of aprepitant by weight, about 1% to about 20% of medium chain triglycerides by weight, about 0.5% to about 5% of emulsifier, tonicity agent and water for injection.

In one general aspect, there is provided an emulsion composition comprising about 0.1% to about 0.13% of aprepitant by weight, about 1% to about 20% of medium chain triglycerides by weight, about 0.5% to about 5% of emulsifier, about 0.1% to about 7% of tonicity agent, water for injection and, optionally, buffering agents.

In one general aspect, there is provided an emulsion composition comprising about 0.1% to about 0.13% of aprepitant by weight, about 1% to about 20% of medium chain triglycerides by weight, about 0.1 to about 5% of lecithin, about 0.1% to about 7% of tonicity agent and water for injection, wherein the tonicity agent is selected from sodium chloride, glycerol, and mannitol.

In one general aspect, there is provided an emulsion composition comprising about 0.1% to about 0.13% of aprepitant by weight, and about 1% to about 20% of an oil selected from the group consisting of structurally modified or hydrolyzed coconut oil, medium chain triglycerides, octyl and decyl glycerate, ethyl oleate, glyceryl linoleate, ethyl linoleate, glyceryl oleate, cholesteryl oleate/linoleate or a mixture thereof.

In one general aspect, there is provided a stable emulsion composition comprising about 0.1% to about 0.13% of aprepitant by weight and about 1% to about 20% of medium chain triglycerides by weight, wherein the emulsion composition is free of ethanol.

In one general aspect, there is provided a stable oil-in-water emulsion composition comprising about 0.1% to about 0.13% of aprepitant by weight and about 1% to about 20% of medium chain triglycerides by weight, wherein the emulsion composition is free of ethanol.

In one general aspect, there is provided a stable emulsion composition comprising about 0.1% to about 0.13% of aprepitant by weight, about 1% to about 20% of medium chain triglycerides by weight, an isotonic agent and one or more pharmaceutically acceptable excipients.

In another general aspect, there is provided an emulsion composition comprising about 0.1% to about 0.13% of aprepitant by weight and about 1% to about 20% of medium chain triglycerides by weight, wherein the composition is characterized in that the dosage form of the composition retains at least 90% w/w of the potency of aprepitant when stored at 25° C. and 60% relative humidity for 3 months, or at 40° C. and 75% relative humidity for 3 months.

In another general aspect, there is provided an emulsion composition comprising about 0.1% to about 0.13% of aprepitant by weight and about 1% to about 20% of medium chain triglycerides by weight, wherein the composition is characterized by a mean globule size not exceeding 500 nm.

In another general aspect, there is provided an emulsion composition comprising about 0.1% to about 0.13% of aprepitant by weight and about 1% to about 20% of medium chain triglycerides by weight, wherein the composition is characterized by a mean globule size being less than 200 nm.

In another general aspect, there is provided an emulsion composition comprising about 0.1% to about 0.13% of aprepitant by weight and about 1% to about 20% of medium chain triglycerides by weight, wherein the composition is characterized by having a negative, a positive or a neutral zeta potential. Preferably, the emulsion has a negative zeta potential.

In one general aspect, there is provided an emulsion composition of aprepitant, wherein the composition does not degrade to impurities associated with the emulsion compositions on storage.

In another general aspect, there is provided an emulsion composition comprising about 0.1% to about 0.13% of aprepitant by weight and about 1% to about 20% of medium chain triglycerides by weight, wherein the aprepitant is soluble at pharmaceutically useful concentrations and stable (i.e., remains chemically unchanged) over significant periods of time.

In another general aspect, a pharmaceutical composition suitable for intravenous administration comprises a stable emulsion comprising an oil phase and an aqueous phase. The oil phase comprises aprepitant, medium chain triglycerides, surfactant and emulsifier or surfactant. The aqueous phase comprises water, a tonicity agent and a pH-adjusting agent or buffer.

In one general aspect, there is provided an emulsion composition, wherein the tonicity agent is about 1% to about 7% by weight, about 1% to about 5% by weight, about 1% to about 3% by weight, or about 0.1% to about 0.9% by weight.

In another general aspect, there is provided a method of administration of aprepitant by infusion, wherein the infusion time is equal to or less than thirty minutes.

In another general aspect, there is provided a method for preparing an emulsion comprising aprepitant that is suitable for parenteral administration.

In another general aspect, there is provided a stable emulsion composition comprising about 0.1% to about 0.13% of aprepitant by weight and about 1% to about 20% of medium chain triglycerides by weight. The composition is characterized in that the dosage form of the composition retains at least 90% w/w of the potency of aprepitant when stored at 25° C. and 60% relative humidity for 3 months or at 40° C. and 75% relative humidity for 3 months.

In another general aspect, there is provided a stable emulsion composition comprising about 0.1% to about 0.13% of aprepitant by weight and about 1% to about 20% of medium chain triglycerides by weight. The composition is free of ethanol and characterized in that the dosage form of the composition retains at least 90% w/w of the potency of aprepitant when stored at 25° C. and 60% relative humidity for 3 months or at 40° C. and 75% relative humidity for 3 months.

In another general aspect, there is provided methods for preparing stable emulsions comprising aprepitant which are suitable for intravenous administration and which can be prepared according to conventional manufacturing procedures using aseptic techniques.

In another general aspect, there is provided methods for preparing stable emulsions comprising aprepitant which are suitable for intravenous administration. The emulsion composition is terminally sterilized in the final container closure system such as bags or glass vials using moist heat.

In another aspect, the emulsion is free of a long chain triglyceride or free of a triglyceride having a fatty acid chain of 14 or more carbons. In another aspect the emulsion is free of a triglyceride having a fatty acid chain of 12 or more carbons.

Still other aspects and advantages of the invention will be apparent from the following detailed description of the invention.

DETAILED DESCRIPTION

It is typically quite desirable for one phase of an emulsion to be substantially uniformly dispersed within the other phase. Such dispersion can significantly affect the capabilities of the emulsion to deliver therapeutic ingredients. Moreover, such a dispersion often provides an indication of the stability of the emulsion itself.

The separate phases of an emulsion can be extremely difficult to evenly disperse throughout a composition since each phase tends to associate with itself rather than the other phase. Also, the maintenance of the distribution of the dispersed phase within the continuous phase can be very delicate. It is also often difficult to include additional ingredients within an emulsion since many ingredients can act to inhibit the dispersion and/or even distribution of the dispersed phase throughout the continuous phase.

Thus the inventors of the present invention have discovered ready-to-use aprepitant emulsion formulations which can be prepared in an entirely solubilized and stable form suitable for administration by intravenous infusion. The inventors of the present invention have prepared an emulsion formulation that will allow aprepitant to be incorporated into an emulsion for intravenous administration and remain stable during the shelf life of the formulation. In particular, the inventors of the present invention have developed an emulsion formulation comprising aprepitant and medium chain triglycerides that can be administer directly by intravenous infusion without any further dilution. The emulsion composition is also free of ethanol in the formulation, which thereby reduces the side effects of ethanol upon administration.

The present invention relates to a stable emulsion formulation of aprepitant administered by intravenous infusion. The emulsion comprises about 0.1% to about 0.13% of aprepitant by weight and 1% to about 20% of medium chain triglycerides by weight. The emulsion is free of ethanol.

The term "aprepitant" used throughout the specification refers to not only aprepitant per se, but also its other pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. In another aspect, the term "aprepitant" refers to aprepitant per se and its pharmaceutically acceptable salts, solvates, and hydrates. It should be understood that the term includes enantiomers and polymorphs.

The terms pharmaceutically acceptable excipients and excipients are used interchangeably in this disclosure. They are generally safe for administering to humans according to established governmental standards, including those promulgated by the United States Food and Drug Administration.

The term "formulation" refers to a mixture of excipients or other chemicals prepared according to a specific recipe and preparation procedure. The terms of "composition" and "formulation" are used interchangeably in this application.

Unless otherwise specifically stated all emulsion ingredient amounts or percentages are weight volume percentages (w/v %).

The emulsion comprises an aqueous phase, which comprises a tonicity agent, an osmotic agent, a pH-adjusting agent, and water.

The emulsion comprises an oil phase, which comprises aprepitant, medium chain triglycerides and emulsifier.

The ratio of emulsifier to aprepitant in the composition ranges from about 3:1 to about 50:1 by weight.

The oil component influences curvature by its ability to penetrate and hence swell the tail region of the surfactant monolayers. Oils with shorter chain length can penetrate the tail region to a greater extent than the oils with longer chain length and hence swell to a greater extent and gives larger emulsion region in the ternary phase diagram, and hence used as medium chain triglycerides in the present invention.

The oil is selected from the group of castor oil, coconut oil, certain triglycerides, octyl and decyl glycerate, ethyl oleate, glyceryl linoleate, ethyl linoleate, glyceryl oleate, cholesteryl oleate/linoleate or a mixture thereof. The oil used in the composition comprises about 1% to about 20%.

The medium chain triglycerides (MCTs) are used as the oil phase in the emulsion composition according to the present invention. Exemplary medium chain triglycerides include but are not limited to 8-10 carbons in length and in some embodiments may include 12 carbons in length. These medium chain triglycerides are metabolized rapidly and more completely than are long-chain triglycerides (LCTs) because they enter the mitochondria of the liver, heart, and kidney for oxidation without first being converted to a carnitine transport form. Moreover, the medium chain triglycerides are preferentially oxidized rather than stored as fat. Their rapid oxidation can eventually lead to ketone formation (acetoacetate and β-hydroxybutyrate) when the acetyl-CoA generated by β-oxidation overwhelms entry into the tricarboxylic acid cycle. The ketone bodies thus produced may serve as an alternate form of energy for body tissues. The more rapid removal of MCTs from blood is consistent with more rapid hydrolysis by lipoprotein lipase and oxidation to carbon dioxide. This more rapid removal and subsequent oxidation to carbon dioxide is more clearly appreciated when one considers the molecular processes that are responsible. By virtue of their improved solubility profile compared with LCTs, MCTs display emulsifier-like properties that improve the stability of emulsion composition.

The ratio of medium chain triglycerides to aprepitant in the composition ranges from about 5:1 to about 200:1.

The tonicity or isotonic agents used in emulsion compositions, are used to adjust the composition of the formulation to the desired isotonic range. Examples thereof include ionic isotonic agents, non-ionic isotonic agents, and the like.

Examples of the ionic isotonic agents include inorganic salts and organic salts.

Examples of the inorganic salts include disodium phosphate, sodium dihydrogen phosphate, potassium dihydrogen phosphate, sodium hydrogen sulfite, sodium sulfite, sodium thiosulfate, magnesium sulfate, sodium chloride, potassium chloride, calcium chloride, magnesium chloride and the like.

Examples of the non-ionic isotonic agents include polyhydric alcohols having two or more alcoholic hydroxy groups in single molecules, and the like.

Specific examples of the polyhydric alcohols include, for example, glycerol, propylene glycol, polyethylene glycol, glucose, trehalose, mannitol, dextrose, sucrose, xylitol, sorbitol, and the like.

Among these isotonic agents, the preferred isotonic agents may include polyhydric alcohols such as glycerin, propylene glycol, and polyethylene glycol; preferably glycerin.

Moreover, one of the isotonic agents in the present invention may be used alone, or two or more thereof may be used in any combination.

Further, the concentration of the isotonic agent in the present invention can be adjusted as appropriate in consideration of the influence on the drug and/or the other additive (s); and the adjustment of the osmotic pressure (osmotic pressure ratio) of the emulsion composition to a particular range. In the case where the isotonic agent in the present invention is a non-ionic isotonic agent, the concentration is for example 10 to 1,000 mmol/L, preferably 20 to 500 mmol/L, more preferably 20 to 300 mmol/L, and particularly preferable is 20 to 200 mmol/L.

In the case of an ionic isotonic agent, the concentration of all ions including cations and anions but not those of the drug is 10 to 1,000 (mmol/L), preferably 20 to 500 (mmol/L), more preferably 20 to 300 (mmol/L), and particularly preferable is 20 to 200 (mmol/L).

Furthermore, in the case where the isotonic agent in the present invention is a non-ionic isotonic agent or a polyhydric alcohol, particularly glycerin, the content can be adjusted as appropriate in consideration of the influence on the drug, the other additive(s), and/or the osmotic pressure of the emulsion composition.

The tonicity agent used in the composition comprises about 0.1% to about 7.0% by weight.

The buffers or pH-adjusting agent in emulsion compositions, used to adjust the pH to a desirable range. Exemplary buffers include, but are not limited to, phosphate buffer, citrate buffer, tris buffer, carbonate buffer, succinate buffer, maleate buffer and borate buffer. In another embodiment, the buffer is selected from the group of phosphate buffered saline (PBS), modified PBS and citrate buffer.

The pH adjusting agent is selected from sodium hydroxide, potassium hydroxide, magnesium hydroxide, sodium carbonate, tris, sodium linoleate, sodium oleate, potassium carbonate, potassium linoleate, potassium oleate, and mixtures thereof. The emulsion composition has a pH of about 5 to 9, 6 to 8, or 5 to 7.

Suitable preservatives according to the invention may include, but are not limited to benzalkonium chloride, methyl and ethyl parabens, hexetidine, phenyl mercuric salts and the like and mixtures thereof. The amounts of preservative components included in the present compositions are such as to be effective in preserving the compositions and can vary based on the specific preservative component employed, the specific application involved, and like factors. Preservative concentrations often are in the range of about 0.00001% to about 0.05% or about 0.1% by weight of the composition, although other concentrations of certain preservatives may be employed.

One of the approaches to stabilize an emulsion is by conferring an electrostatic charge to the droplet surface which will result in droplet repulsion and less droplet coalescence. Depending on the nature of the film substances, the external surface of the colloid particles may be charged. Colloidal particles dispersed in a solution are electrically charged due to their ionic characteristics and dipole attributes. This charge, which can be negative resulting in anionic emulsions or positive producing cationic emulsions (Klang et al., Pharm. Dev. Technology 2000, 5, 521-532) is known in the art as the "zeta potential" and is a measure of the magnitude of the repulsion or attraction between particles.

The emulsion composition of the invention is characterized by having a negative zeta potential in the range of between −1 mV and −50 mV.

Zeta potential measurements may be carried out by various methods known in the art.

The stability of the emulsions is assessed by measuring physicochemical parameters such oil droplet size, zeta potential and aprepitant content after sterilization by autoclave or filtration and during an accelerated stability test.

Emulsions for intravenous administration should have a very small droplet size to circulate in the bloodstream without causing capillary blockage and embolization. These size limits are characterized by USP33-NF28 General Chapter 729 for Globule Size Distribution in Lipid Injectable Emulsions, herein after referred to as USP 729, which defines universal limits for (1) mean droplet size not exceeding 500 nm or 0.5 μm and (2) the population of large-diameter fat globules, expressed as the volume-weighted percentage of fat greater than 5 μm not exceeding 0.05%, irrespective of the final lipid concentration.

As the droplet size and surface properties are the important parameters for the evaluation of the stability of any colloidal systems.

The mean globule size of the emulsion is less than 1,000 nm, preferably less than 500 nm, more preferably less than 200 nm.

The aprepitant emulsion according to the present invention is prepared by a method comprising the following steps: (1) preparing an oil phase by dissolving aprepitant, an emulsifier and oil; (2) preparing an aqueous phase by mixing water, tonicity agent and or an osmotic agent and optionally with a pH modifier and optionally with a buffer; (3) combining the oil phase and the aqueous phase and subjecting this to high speed homogenization to generate a crude emulsion; and (4) subjecting the crude emulsion to high pressure homogenization to generate a fine emulsion. It is this emulsion that may be administered directly to a patient by intravenous infusion without further dilution.

It is to be understood that the above description is intended to be illustrative and not restrictive. Many embodiments and variations will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

Example 1

| Sr. No | Name of ingredients | Percentage (w/v) |
| --- | --- | --- |
| 1 | Aprepitant | 0.1-0.13 |
| 2 | Lecithin | 0.5-5.0 |
| 3 | Medium chain triglycerides | 1-20 |
| 4 | Glycerol | 1-3 |
| 5 | Water for injection | Q.S. to desired quantity |

Procedure:
1. In a suitable container take the required amount of medium chain triglycerides.
2. Add the required quantity of lecithin to the medium chain triglycerides and mix until complete dissolution.
3. Add the required quantity of aprepitant to the mixture and mix until complete dissolution.
4. In a separate container take the required quantity of water for injection.
5. Add the required quantity of glycerol or other suitable tonicity modifier to the water for injection and mix until complete dissolution.
6. Slowly add the aqueous phase to the oil phase under high shear mixing to form a coarse emulsion.
7. Subject the coarse emulsion to high pressure homogenization under suitable conditions in order to reduce the globule size to a value below 200 nm.
8. Collect the final emulsion, fill into suitable containers and close the openings of the filled containers.
9. Subject the filled containers to terminal sterilization using moist heat.

Example 2

| Sr. No | Name of ingredients | Percentage (w/v) |
| --- | --- | --- |
| 1 | Aprepitant | 0.1-0.13 |
| 2 | Lecithin | 0.5-5.0 |
| 3 | Medium chain triglycerides | 1-20 |
| 4 | Sodium chloride | 0.1-0.9 |
| 5 | Water for injection | Q.S. to desired quantity |

Procedure:
1. In a suitable container take the required amount of medium chain triglycerides.
2. Add the required quantity of lecithin to the medium chain triglycerides and mix until complete dissolution.
3. Add the required quantity of aprepitant to the mixture and mix until complete dissolution.
4. In a separate container take the required quantity of water for injection.
5. Add the required quantity of sodium chloride or other suitable tonicity modifier to the water for injection and mix until complete dissolution.
6. Slowly add the aqueous phase to the oil phase under high shear mixing to form a coarse emulsion.

7. Subject the coarse emulsion to high pressure homogenization under suitable conditions in order to reduce the globule size to a value below 200 nm.
8. Collect the final emulsion, fill into suitable containers and close the openings of the filled containers.
9. Subject the filled containers to terminal sterilization using moist heat.

Example 3

| Sr. No | Name of ingredients | Percentage (w/v) |
|---|---|---|
| 1 | Aprepitant | 0.1-0.13 |
| 2 | Lecithin | 0.5-5.0 |
| 3 | Medium chain triglycerides | 1-20 |
| 4 | Dextrose | 1-5 |
| 5 | Water for injection | Q.S. to desired quantity |

Procedure:
1. In a suitable container take the required amount of medium chain triglycerides.
2. Add the required quantity of lecithin to the medium chain triglycerides and mix until complete dissolution.
3. Add the required quantity of aprepitant to the mixture and mix until complete dissolution.
4. In a separate container take the required quantity of water for injection.
5. Add the required quantity of dextrose or other suitable tonicity modifier and mix with the water for injection until complete dissolution.
6. Slowly add the aqueous phase to the oil phase under high shear mixing to form a coarse emulsion.
7. Subject the coarse emulsion to high pressure homogenization under suitable conditions in order to reduce the globule size to a value below 200 nm.
8. Collect the final emulsion, fill into suitable containers and close the openings of the filled containers.
9. Subject the filled containers to terminal sterilization using moist heat.

Example 4

| Sr. No | Name of ingredients | Percentage (w/v) |
|---|---|---|
| 1 | Aprepitant | 0.1-0.13 |
| 2 | Lecithin | 0.5-5.0 |
| 3 | Medium chain triglycerides | 1-20 |
| 4 | Mannitol | 1-7 |
| 5 | Water for injection | Q.S. to desired quantity |

Procedure:
1. In a suitable container take the required amount of medium chain triglycerides.
2. Add the required quantity of lecithin to the medium chain triglycerides and mix until complete dissolution.
3. Add the required quantity of aprepitant to the mixture and mix until complete dissolution.
4. In a separate container take the required quantity of water for injection.
5. Add the required quantity of mannitol or other suitable tonicity modifier to the waer for injection and mix until complete dissolution.
6. Slowly add the aqueous phase to the oil phase under high shear mixing to form a coarse emulsion.
7. Subject the coarse emulsion to high pressure homogenization under suitable conditions in order to reduce the globule size to a value below 200 nm.
8. Collect the final emulsion, fill into suitable containers and close the openings of the filled containers.
9. Subject the filled containers to terminal sterilization using moist heat.

The aprepitant emulsion compositions may consist of aprepitant, lecithin, one or more medium chain triglycerides, water for injection and one or more of mannitol, glycerol, dextrose or sodium chloride. The aprepitant emulsion compositions may consist essentially of aprepitant, lecithin, one or more medium chain triglycerides, water for injection and one or more of mannitol, glycerol, dextrose or sodium chloride. The aprepitant emulsion compositions may comprise aprepitant, lecithin, one or more medium chain triglycerides, water for injection and one or more of mannitol, glycerol, dextrose or sodium chloride.

The aprepitant emulsion compositions may consist of aprepitant at 0.1-0.13% w/v, lecithin at 0.5-5.0% w/v, one or more medium chain triglycerides at 1-20% w/v, water for injection and one or more of mannitol 1-7% w/v, glycerol 1-3% w/v, dextrose 1-5% w/v or sodium chloride at 0.1-0.9% w/v. The aprepitant emulsion compositions may consist essentially of aprepitant at 0.1-0.13% w/v, lecithin at 0.5-5.0% w/v, one or more medium chain triglycerides at 1-20% w/v, water for injection and one or more of mannitol 1-7% w/v, glycerol 1-3% w/v, dextrose 1-5% w/v or sodium chloride at 0.1-0.9% w/v. The aprepitant emulsion compositions may comprise aprepitant at 0.1-0.13% w/v, lecithin at 0.5-5.0% w/v, one or more medium chain triglycerides at 1-20% w/v, water for injection and one or more of mannitol 1-7% w/v, glycerol 1-3% w/v, dextrose 1-5% w/v or sodium chloride at 0.1-0.9% w/v.

The aprepitant compositions may be free of either or both of ethanol and a long chain triglyceride such as soybean oil, and its use may be free of a dilution step prior to intravenous infusion.

The claimed invention is:

1. A ready-to-use emulsion formulation of aprepitant for administration by intravenous infusion, wherein the emulsion consists of:
   about 0.1% to about 0.13% of aprepitant by weight;
   about 1% to about 20% by weight of medium chain triglycerides;
   about 0.5% to about 5.0% by weight of lecithin emulsifier;
   a tonicity agent selected from the group consisting of sodium chloride, glycerol, and mannitol; and
   water for injection,
   wherein the composition is free of long chain triglycerides and ethanol, and
   wherein the emulsion remains stable at 25° C. and 60% relative humidity or at 40° C. and 75% relative humidity for 3 months.

2. The emulsion composition of claim 1, wherein the composition is an oil-in-water emulsion.

3. The emulsion composition of claim 1, wherein the medium chain triglycerides comprises about 1% to about 20% by weight of the composition.

4. The emulsion composition of claim 1, wherein the ratio of lecithin emulsifier to aprepitant in the composition ranges from about 3:1 to about 50:1 by weight.

5. The emulsion composition of claim 1, wherein the tonicity agent is about 0.1% to about 7.0% by weight of the composition.

6. The emulsion composition of claim 1, wherein the composition has a pH of about 5-7.

7. The emulsion composition of claim 1, wherein the emulsion is characterized by having a negative zeta potential.

8. The emulsion composition of claim 1, wherein the droplet of said emulsion has a mean globule size of about 100 nm to about 500 nm.

9. An emulsion composition consisting of:
about 0.1% to about 0.13% by weight of aprepitant;
about 1% to about 20% by weight of medium chain triglycerides;
about 0.5% to about 5.0% by weight of lecithin;
a tonicity agent selected from the group consisting of sodium chloride, glycerol, and mannitol, wherein the tonicity agent comprises about 0.1% to about 7.0% by weight of the composition; and
water for injection
wherein the composition is free of long chain triglycerides and ethanol, has a pH of between 5 and 7, and the emulsion remains stable at 25° C. and 60% relative humidity or at 40° C. and 75% relative humidity for 3 months.

10. A method for treating nausea and vomiting in a subject in need thereof comprising administering a ready-to-use emulsion by intravenous infusion without a step of first diluting the emulsion, wherein the emulsion composition consists of:
about 0.1% to about 0.13% of aprepitant by weight;
about 1% to about 20% by weight of medium chain triglycerides;
about 0.5% to about 5.0% by weight of lecithin;
a tonicity agent selected from the group consisting of sodium chloride, glycerol, and mannitol; and
water for injection,
wherein the composition is free of ethanol and long chain triglycerides, has a pH of between 5 and 7, and the emulsion remains stable at 25° C. and 60% relative humidity or at 40° C. and 75% relative humidity for 3 months.

11. The method according to claim 10, wherein the nausea and vomiting is chemotherapy-induced nausea and vomiting.

12. A process for the preparation of the emulsion composition of claim 1, the process comprising forming an emulsion.

13. The process for preparation of claim 12, further comprising terminally sterilizing a container containing the composition in the final container using moist heat.

14. The process for preparation of claim 12, the process comprising:
(1) preparing an oil phase by dissolving the aprepitant, the lecithin, and the medium chain triglyceride;
(2) preparing an aqueous phase by mixing water and the tonicity agent;
(3) combining the oil phase and the aqueous phase and subjecting the resulting mixture to high speed homogenization to generate a crude emulsion; and
(4) subjecting the crude emulsion to high pressure homogenization to generate a fine emulsion.

15. The process for preparation of claim 14, further comprising filling the emulsion into a container and terminally sterilizing the container using moist heat.

* * * * *